Dec. 17, 1974 W. A. WARRINER Plant Pat. 3,665
ROSE PLANT
Filed Dec. 6, 1973
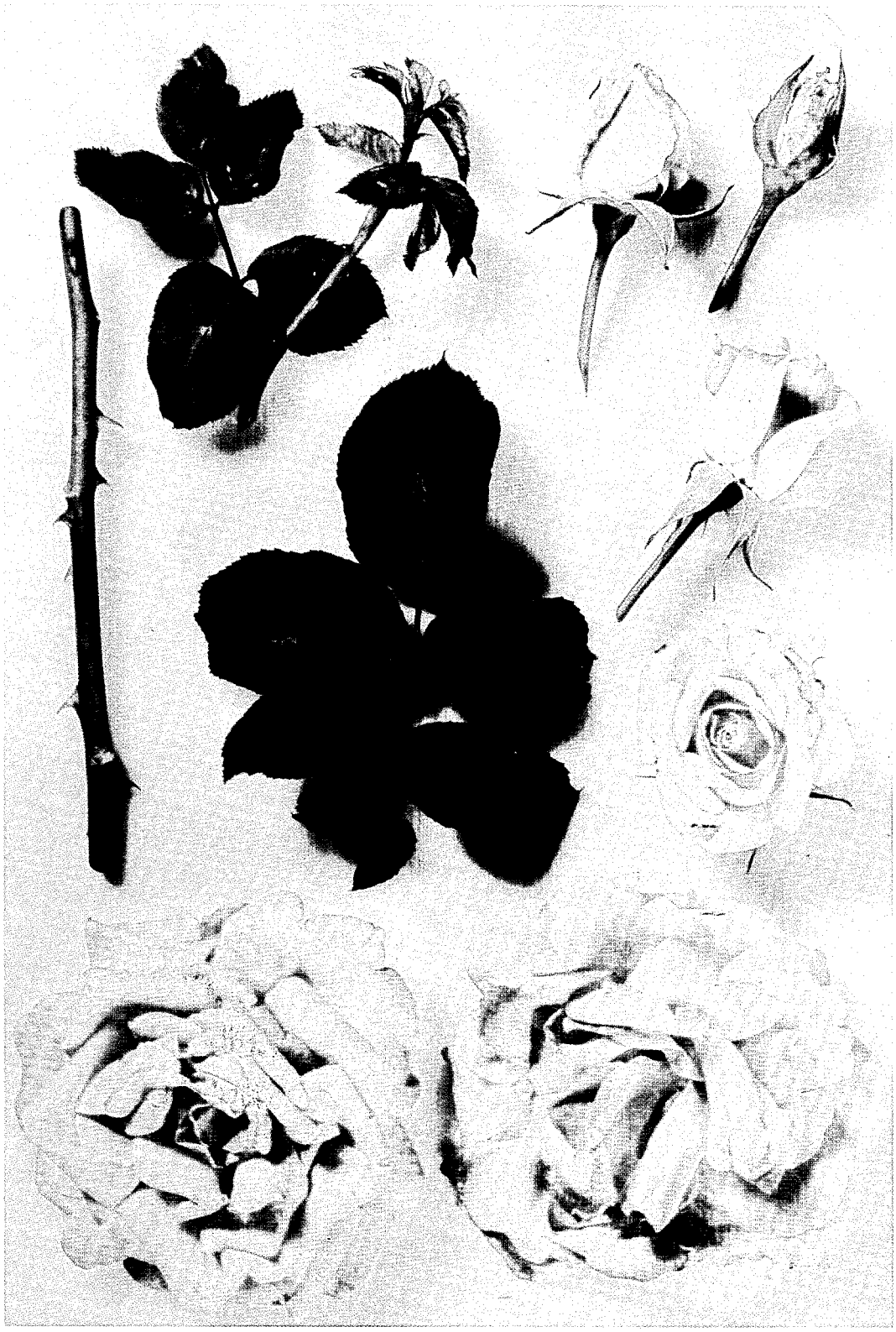

United States Patent Office

Plant Pat. 3,665
Patented Dec. 17, 1974

3,665
ROSE PLANT

William A. Warriner, Tustin, Calif., assignor to Jackson & Perkins Company, Medford, Oreg.

Filed Dec. 6, 1973, Ser. No. 422,171
Int. Cl. A01h 5/00
U.S. Cl. Plt.—19 1 Claim This present invention relates to a new and distinct cultivar of rose plant of the hybrid tea class which was originated by me by crossing the cultivar Tiffany U.S. Plant Pat. 1,304, with pollen from the cultivar South Seas, U.S. Plant Pat. 2,184.

The primary objective of this breeding was to produce a new rose cultivar similar to South Seas in vigor and plant habit with a flower color in the pink range. This objective was substantially achieved along with other desirable improvements as evidenced by the following unique combination of characteristics which are outstanding in the new cultivar and which distinguish it from its parents as well as from all other cultivars of which I am aware.

1. A vigorous, upright habit of growth more like that of South Seas than of Tiffany.
2. A uniform color in all petals of the flower of Camellia rose, which deepens slightly with age. Color is between that of Tiffany and South Seas, showing very little of the yellow of Tiffany and only a little of the darkening effect of South Seas.
3. Very little fragrance.

Asexual reproduction of this new cultivar by budding, as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with *Wilson's Horticultural Color Chart*, except where ordinary dictionary significance of color is indicated.

Parentage: Seedling.
*Seed parent.*—Seedling of Tiffany, U.S. Plant Pat. 1,304.
*Pollen Parent.*—South Seas U.S. Plant Pat. 2,184.
Classification:
*Botanical.*—Rosa hybrid.
*Commercial.*—Hybrid tea.

FLOWER

Observations were made at Irvine, Calif., in late August.

Blooming habit: Recurrent, continuous.
Bud:
*Size.*—1¼" to 1½" when petals start to unfurl.
*Form.*—Pointed, ovoid.
*Color.*—When sepals first divide—near Neyron Rose (623) to (623/1). When half blown; upper side of petals near Camellia Rose (622/1) with a sharply defined area at the base of Primrose Yellow (601/1); lower side of petals near Camellia Rose (622/2) to (622/3) yellow area at base not sharply defined.
*Sepals.*—Color: Outer surface Scheeles Green (860/2). Inner surface nearly covered with white tomentum. Three appendaged sepals lightly appendaged. Two unappendaged sepals hairy edged.
*Receptacle.* — Color: Scheeles Green (860/2). Shape: Funnel. Size: Large, broad. Surface: Smooth.
*Peduncle.*—Length: Medium. Surface: Glandular. Color: Light green. Strength: Slightly bending.
*Opening.*—Slowly, outer petals slightly quilled.

Bloom:
*Size.*—Large. Average size when fully expanded 4".
*Borne.*—Mostly singly.
*Stems.*—Long, strong.
*Form.*—When first open, high center. Permanence—outer petal edges slightly curled.
*Petalage.*—Number of petals under normal conditions 40–50.
*Color.*—Center of flower: Upper side of petals near Camellia Rose (622/1). Reverse side of petals near Camellia Rose (622/2 to 622/3). Outer petals: Upper side of petals near Camellia Rose (622/2 to 622/3). Reverse of petals near Camellia Rose (622/2 to 622/3). Base of petals—Primrose yellow (601/1). General tonality from a distance—Camellia Rose (622/1).
Discoloration.—General tonality at end of first day—no change. Third day—exposed areas age to near Neyron Rose (623) or occasionally darker.
*Fragrance.*—None.
*Petals.*—Texture—Thin. Surface—Inside, satiny. Reverse, satiny.
*Shape.*—Deltoid.
*Form.*—Edges slightly quilled.
*Arrangement.*—Imbricated.
*Petaloids in center.*—Few, large.
*Persistence.*—Drop off cleanly.
*Lastingness.*—On the plant—long. As cut flower—long.
Reproductive parts:
*Stamens, anthers.*—Medium. Color—yellow. Arrangement—regular around styles.
*Filaments (threads).*—Long and medium. Color—yellow.
*Pollen.*—Lemon yellow.
*Styles.*—Color—near white.
*Stigmas.*—Color—near white.
Fruit: Not observed.

PLANT

Form: Bush.
Growth: Vigorous, upright.
Foliage: Number of leaflets on normal mid-stem leaves, 5–7.
*Size.*—Large.
*Quantity.*—Normal.
*Color.*—New foliage: Near Garnet Brown (00918/3). Old foliage: Near Parsley Green (00962/1).
Leaflets:
*Shape.*—Oval.
*Texture.*—Leathery.
*Edge.*—Serrated.
*Serration.*—Single, small.
*Petiole (rachis).* — Color — green. Underside—prickles.
*Stipules.*—Long, bearded.
*Disease Resistance.*—Slightly susceptible to blackspot under normal growing conditions at Irvine, Calif.
Wood:
*New Wood.*—Light green.
*Bark.*—Smooth.
*Old Wood.*—Green.
*Bark.*—Smooth.

Prickles:

*Quantity.*—On main stalks from base—few. On laterals from stalk—few.

*Form.*—Broad base, hooked downward.

*Color when young.*—Brown.

*Position.*—Irregular.

Small Prickles:

*Quantity.*—On main stalks—few. On laterals—few.

*Color.*—Brown.

I claim:

1. A new and distinct cultivar of rose plant of the hybrid tea class, substantially as herein shown and described, characterized particularly as to novelty by the unique combination of its upright and well branched habit of growth; its uniform, long lasting flower color, its lack of strong flower fragrance.

No references cited.

ROBERT E. BAGWILL, Primary Examiner